United States Patent
Yin

(10) Patent No.: US 11,559,476 B2
(45) Date of Patent: Jan. 24, 2023

(54) HYDROGEL AND METHOD FOR PREPARING THE SAME

(71) Applicant: BOE Technology Group Co., Ltd., Beijing (CN)

(72) Inventor: Yudan Yin, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 105 days.

(21) Appl. No.: 16/913,323

(22) Filed: Jun. 26, 2020

(65) Prior Publication Data

US 2020/0405608 A1     Dec. 31, 2020

(30) Foreign Application Priority Data

Jun. 27, 2019 (CN) .................. 201910567716.2

(51) Int. Cl.

| | |
|---|---|
| *A61K 8/60* | (2006.01) |
| *A61K 47/69* | (2017.01) |
| *A61K 47/54* | (2017.01) |
| *A61K 9/06* | (2006.01) |
| *A61K 31/715* | (2006.01) |
| *A61Q 19/00* | (2006.01) |

(52) U.S. Cl.
CPC .................. *A61K 8/60* (2013.01); *A61K 9/06* (2013.01); *A61K 31/715* (2013.01); *A61K 47/549* (2017.08); *A61K 47/6911* (2017.08); *A61Q 19/00* (2013.01)

(58) Field of Classification Search
CPC .............. A61K 47/6903; A61K 47/549; A61K 47/6911; A61K 31/715; A61K 47/26; A61K 9/0014; A61K 9/06; A61K 9/1271; A61K 8/60; A61K 8/042; A61K 8/606; A61Q 19/00
See application file for complete search history.

(56) References Cited

FOREIGN PATENT DOCUMENTS

| | | |
|---|---|---|
| CN | 101089004 A | 12/2007 |
| CN | 101744768 A | 6/2010 |
| CN | 103232510 A | 8/2013 |
| CN | 103976941 A | 8/2014 |
| CN | 107496358 A | 12/2017 |

OTHER PUBLICATIONS

Over Chiaki Yoshina-Ishii et al., "General Method for Modification of Liposomes for Encoded Assembly on Supported Bilayers," in JACS Communications, 2005, pp. 1357-1358 (Year: 2005).*
Son (WO 2017196077 A1, using Eng. Trans. (Year: 2017).*

(Continued)

*Primary Examiner* — Blessing M Fubara
(74) *Attorney, Agent, or Firm* — Nath, Goldberg & Meyer; Joshua B. Goldberg

(57) ABSTRACT

The present application provides a method for preparing a hydrogel and the obtained hydrogel. The method including: forming a first part by mixing a first single-stranded nucleotide with a first liposome, and forming a second part by mixing a second single-stranded nucleotide with a second liposome, wherein the first single-stranded nucleotide and the second single-stranded nucleotide have complementary sticky ends; forming a hydrogel by mixing the first part and the second part.

11 Claims, 2 Drawing Sheets

(56) References Cited

OTHER PUBLICATIONS

Silvia Catuogno et al., ("Aptamer-Mediated Targeted Delivery of Therapeutics: An Update" in Pharmaceutics, 2016, pp. 1-24). (Year: 2016).*
First Office Action dated Dec. 16, 2021 for application No. CN 201910567716.2 with English translation attached.
Yoshina-Ishii, Chiaki, et al.; "General Method for Modification of Liposomes for Encoded Assembly on Supported Bilayers"; Nov. 7, 2004; Department of Chemistry, Stanford University, Stanford, California.
Godeau,Guilhem, et al.; "Glycosyl-Nucleoside Lipids as Low-Molecular-Weight Gelators"; Mar. 20, 2009; Bordeaux, France.
Gissot, Arnaud, et al.; "Nucleoside, nucleotide and oligonucleotide based amphiphiles: a successful marriage of nucleic acids with lipids"; Mar. 5, 2008; Bordeaux, France.
Yang, Yanfang, et al.; Thermal and magnetic dual-responsive liposomes with a cell-penetrating peptide-siRNA conjugate for enhanced and targeted cancer therapy; Jul. 2, 2016; Beijing, China.

\* cited by examiner

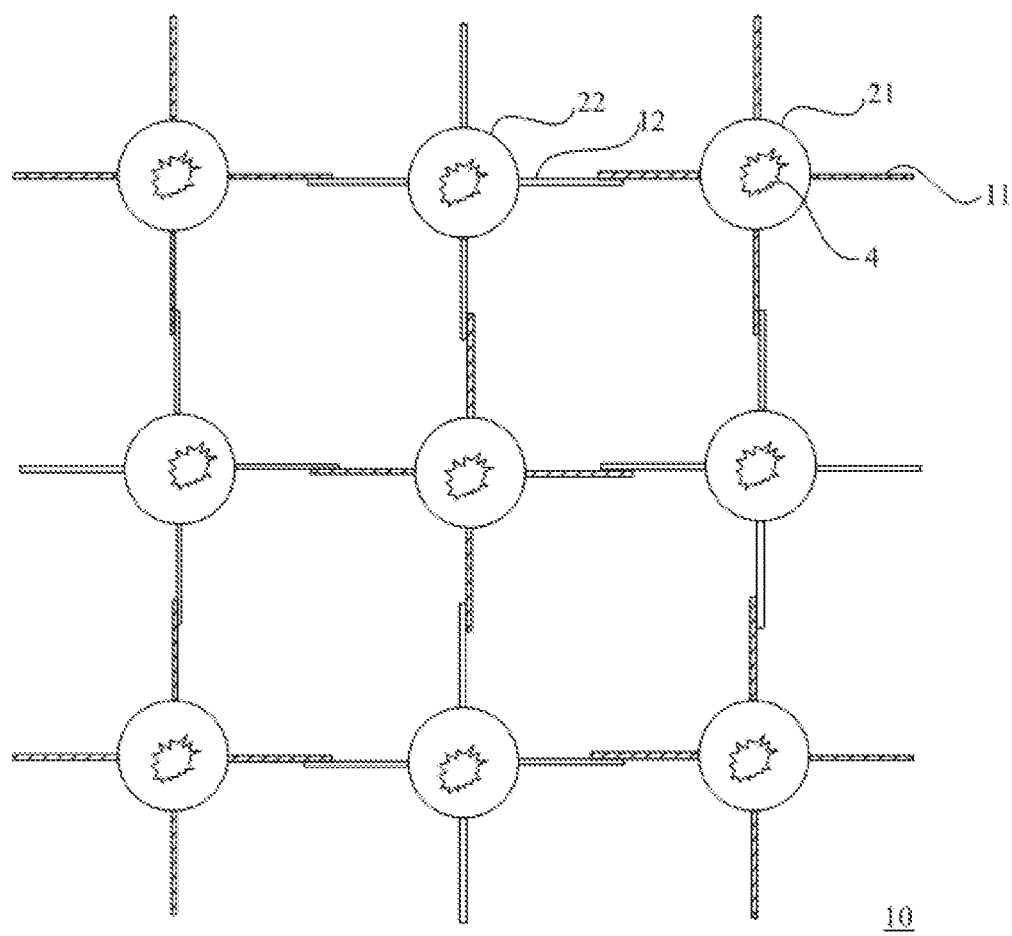

Figure 1 forming a first part by mixing a first single-stranded nucleotide with a first liposome, and forming a second part by mixing a second single-stranded nucleotide with a second liposome, wherein the first single-stranded nucleotide and the second single-stranded nucleotide have complementary sticky ends — S11 forming a hydrogel by mixing the first part and the second part — S12

Figure 2

HYDROGEL AND METHOD FOR PREPARING THE SAME

CROSS REFERENCE TO RELATED APPLICATION

This application claims priority to China Application Serial No. 201910567716.2 filed on Jun. 27, 2019, the disclosure of which is hereby incorporated in its entirety by reference.

TECHNICAL FIELD

The invention belongs to the field of biomedical technology, and particularly relates to a hydrogel and a method for preparing the same.

BACKGROUND TECHNIQUE

Hydrogel generally refers to polymers containing hydrophilic groups and being capable of maintain their complete three-dimensional network structures after swollen by water. Hydrogel has widespread application prospects in the field of biomedicine since it has a structure similar to the extracellular matrix.

For example, hydrogel is used to encapsulate drugs for external application. However, the existing hydrogels in the prior art cannot control the release of the drugs well, such as too fast release of drugs.

SUMMARY OF THE INVENTION

The present application at least partially solves the problem that the existing hydrogels release load materials too fast, and provides a hydrogel that could release load materials slowly.

In one aspect, the present application provides a hydrogel comprising a plurality of first single-stranded nucleotides, a plurality of first liposomes, a plurality of second single-stranded nucleotides, and a plurality of second liposomes, wherein the first single-stranded nucleotides and the second single-stranded nucleotides have complementary sticky ends.

Optionally, the first single-stranded nucleotide and the second single-stranded nucleotide are both single-stranded oligonucleotides (ss-oligo DNA).

Optionally, the hydrogel further includes a linker.

Optionally, the first or second liposomes contain a load material, and the load material is a medicine or a cosmetic.

In another aspect, the present application provides a method for preparing a hydrogel, including:

forming a first part by mixing a first single-stranded nucleotide with a first liposome, and forming a second part by mixing a second single-stranded nucleotide with a second liposome, wherein the first single-stranded nucleotide and the second single-stranded nucleotide have complementary sticky ends;

forming a hydrogel by mixing the first part and the second part.

Optionally, the first single-stranded nucleotide and the second single-stranded nucleotide are both single-stranded oligonucleotides.

Optionally, before forming the first part and the second part, the method further includes: mixing a load material with the first liposome and/or the second liposome respectively, so as to making the first liposome and/or the second liposome encapsulate the load material.

Optionally, the load material is a medicine or a cosmetic.

Optionally, after forming a hydrogel by mixing the first part and the second part, the method further includes: releasing at least part of the load material from the first liposome and the second liposome by adding a surfactant to the hydrogel.

Optionally, forming the first part and forming the second part include: mixing the first single-stranded nucleotide, the first liposome and a linker, and connecting the first single-stranded nucleotide with the first liposome through the linker to obtain the first part; mixing the second single-stranded nucleotide, the second liposome and a linker, and connecting the second single-stranded nucleotide with the second liposome through the linker to obtain the second part.

Optionally, the linker is a cell-penetrating peptide.

DESCRIPTION OF THE FIGURES

FIG. 1 is a schematic structure diagram of the hydrogel according to the present application;

FIG. 2 is a schematic flow chart of one embodiment of the method for preparing a hydrogel according to the present application;

DETAILED DESCRIPTION OF EMBODIMENTS

Figure 3:
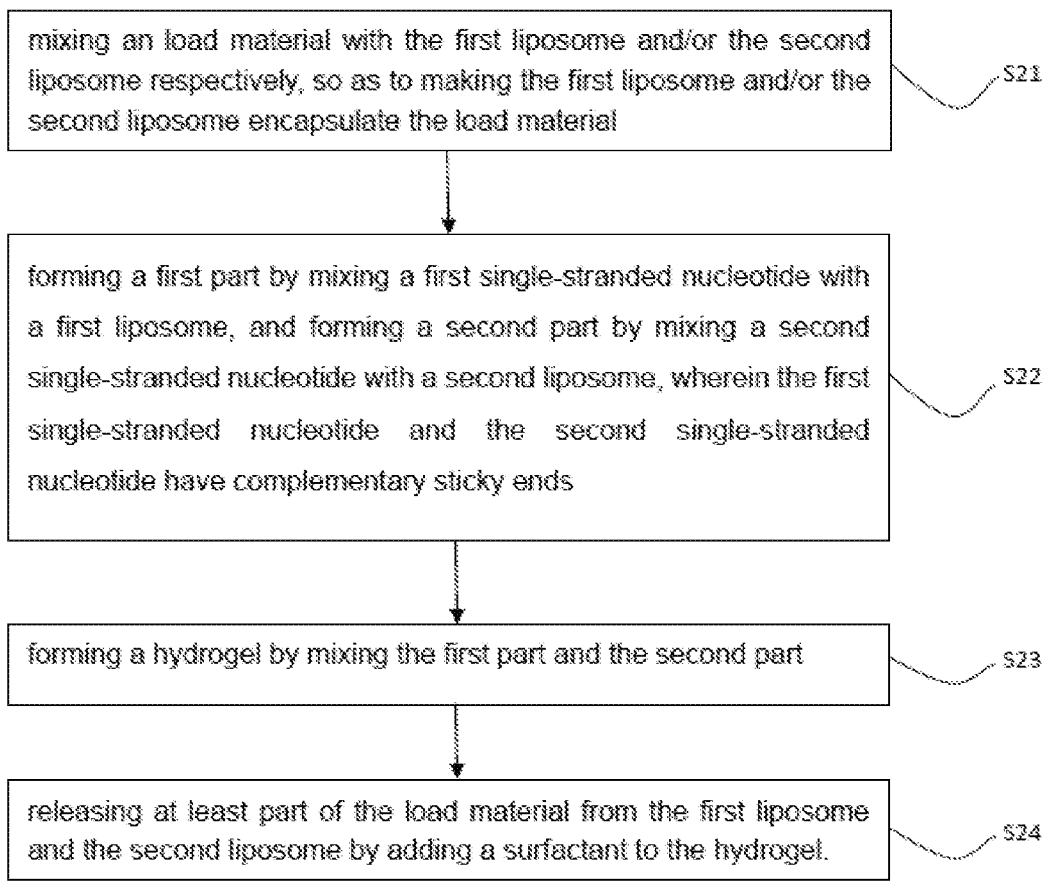
FIG. 3 is a schematic flow chart of another embodiment of the method for preparing a hydrogel according to the present application.

In order to enable those skilled in the art to better understand the technical solutions of the present application, the present application will be described in further detail below with reference to the accompanying drawings and specific embodiments.

The present application will be described in more detail below with reference to the drawings. In the various drawings, the same elements are denoted by similar reference numerals. For clarity, various parts in the drawings are not drawn to scale. In addition, some well-known parts may not be shown in the drawings.

In the following, many specific details of the present application are described, such as structures, materials, dimensions, treatment processes and techniques of the components, in order to understand the present application more clearly. However, as can be understood by those skilled in the art, the present application may be implemented not according to these specific details.

According to some embodiments of the present application, as shown in FIG. 1, the hydrogel includes a plurality of first single-stranded nucleotides 11, a plurality of second single-stranded nucleotides 12, a plurality of first liposomes 21 and a plurality of second liposomes 22, wherein the first single-stranded nucleotide and the second single-stranded nucleotide have complementary sticky ends.

Ratio of the single-stranded nucleotides to the liposomes will be adjusted depending on factors such as natures of the liposomes, and size and sequence of the nucleotides in the single-stranded nucleotides. Those skilled in the art can select appropriate liposomes and nucleotides according to the requirements of specific applications.

Optionally, the first single-stranded nucleotide and the second single-stranded nucleotide are both single-stranded oligonucleotides.

When the liposome contacts water, a hydrophilic head of phospholipid molecule is inserted into water and a hydrophobic tail of the liposome extends into the air, thereby forming a spherical liposome with double-layered lipid molecules which has a diameter of 25 nm to 1000 nm. Liposomes in pharmacy generally refer to micro vesicular bodies formed by lipid-like bilayers encapsulating drugs.

The first liposome 21 and the second liposome 22 may be the same liposome material or different liposome materials.

Optionally, the hydrogel further includes a linker.

Optionally, the first or second liposome contains a load material, and the load material may be a medicine or a cosmetic.

The load material 4 may be a skin care product for moisturizing the skin. The hydrogel 10 is placed on human skin that needs to be moisturized, and the load material 4 in the liposome is released onto the skin and then moisturizes the skin. That is, the load material 4 is a skin care product for moisturizing, and the hydrogel 10 correspondingly is a facial mask.

The load material 4 may also be a medicine. The hydrogel 10 comprising a medicine as the load material 4 is placed on human skin having a disease, and the medicine in the liposome is released onto the skin and then could play a therapeutic role on the skin having a disease.

Some embodiments of the present application provide a method for preparing a hydrogel, including:

forming a first part by mixing a first single-stranded nucleotide 11 with a first liposome 21, and forming a second part by mixing a second single-stranded nucleotide 12 with a second liposome 22, wherein the first single-stranded nucleotide and the second single-stranded nucleotide have complementary sticky ends;

forming a hydrogel by mixing the first part and the second part.

The first single-stranded nucleotide in the first part is connected to the first liposome, and the second single-stranded nucleotide in the second part is connected to the second liposome. The sticky ends of the first single-stranded nucleotide connect to the stick ends of the second single-stranded nucleotide so that the first part and the second part are paired with each other to form a hydrogel product. Therefore, the first part and the second part can be regarded as intermediate products of the hydrogel.

In the obtained hydrogel, a sticky end of the first single-stranded nucleotide 11 combines with a sticky end of the second single-stranded nucleotide 12 to form a new single-stranded nucleotide. Each first liposome 21 connects with one or more first single-stranded nucleotides 11, each second liposome 22 connects with one or more second single-stranded nucleotides 12. The connection of the first and second single-stranded nucleotides makes the first liposome and the second liposome to be linked together by the resulting new single-stranded nucleotide. Connections of a plurality of first single-stranded nucleotides and a plurality of second single-stranded nucleotides make a plurality of first and second liposomes to be connected together by a network of single-stranded nucleotides.

Optionally, the first single-stranded nucleotide and the second single-stranded nucleotide are both single-stranded oligonucleotides.

As mentioned above, ratio of the single-stranded nucleotides to the liposomes in the first and second parts will be adjusted depending on factors such as natures of the liposomes, and sizes and sequences of the nucleotides in the single-stranded nucleotides.

Specifically, when the first liposome 21 is a DPPC/DPPG liposome, if the concentration of the first liposome 21 is 1 mg/ml, the corresponding concentration range of the first single-stranded nucleotide 11 may be 0.05 mg/mL-1.0 mg/ml.

Mixing of the single-stranded nucleotides and liposomes can be performed at a phase transition temperature of the liposomes or at a temperature 2 or 3° C. higher than the phase transition temperature for 15-30 minutes. For example, mixing temperature is the phase transition temperature of the first liposome 21, or 2 or 3° C. higher than the phase transition temperature of the first liposome 21; and mixing time is 15 to 30 minutes. Mixing conditions of the second single-stranded nucleotide 12 and the second liposome 22 are similar to those of the first single-stranded nucleotide and the first liposome.

The first part and the second part are mixed generally under a standard that the first liposome and the second liposome have the same concentration and the same volume. In other words, the molar mass ratio of the first liposome 21 and the second liposome 22 should be 1:1.

The first part and the second part are mixed at a temperature 2 or 3° C. lower than the phase transition temperature of the first liposome 21 and the second liposome 22. For example, when both the first liposome 21 and the second liposome 22 are DPPC liposomes, the mixing is carried out at a temperature of 37° C.

Optionally, before forming the first part and the second part, the method further includes: mixing a load material with the first liposome and/or the second liposome respectively, so as to make the first liposome and the second liposome encapsulate the load material. The load material in the first liposome and the second liposome may be the same or different.

Optionally, the load material is a medicine or a cosmetic.

Encapsulation rate of the load material in the liposomes will depend on natures of the liposomes (eg, electrical properties, composition of phospholipids, dopants, etc.), natures of the load material (eg, electrical properties, hydrophilicity, hydrophobicity, molecular size, etc.) and the way of encapsulation. The encapsulation rate of the load material in liposomes is generally 1% to 100%, The encapsulation rates of the load material in the first liposomes and the second liposomes may be the same or different.

The way of encapsulation can be a variety of ways that can be realized, such as a film-forming hydration method. The film-forming hydration method is usually performed by 2 hours of hydration using a rotary evaporator at a reaction temperature greater than the phase transition temperature of the liposomes. For example, if the liposome is DPPC/DPPG liposome and the phase transition temperature thereof is 41° C., the reaction temperature is preferably 60° C.; if the liposome is lecithin, the reaction temperature may be room temperature.

Optionally, forming the first part and forming the second part include: mixing the first single-stranded nucleotide, the first liposome and a linker, and connecting the first single-stranded nucleotide with the first liposome through the linker to obtain the first part; mixing the second single-stranded nucleotide, the second liposome and a linker, and connecting the second single-stranded nucleotide with the second liposome through the linker to obtain the second part.

Optionally, the linker is a cell-penetrating peptide.

Optionally, after forming the hydrogel by mixing the first part and the second part, the method further includes: releasing at least part of the load material from the first liposome and the second liposome by adding a surfactant to the hydrogel.

The surfactant releases the load material by denaturation of the first liposome and the second liposome, and the releasing ability of the first liposome 21 and the second liposome 22 can be adjusted by controlling the addition amount of the surfactant. If more releasing of the load material 4 is needed, more surfactants may be added to increase the denaturation degree of the first liposome 21 and the second liposome 22 (e.g., higher degree of liposome lysis), so that more of the load material 4 is released. If less releasing of the load material 4 is needed, less surfactants may be added to reduce the denaturation degree of the first liposome 21 and the second liposome 22 (e.g., lower degree of liposome lysis), so that a slow release of the load material 4 is achieved.

The surfactant may be a non-ionic surfactant of Triton X-100, or an ionic surfactant of SDS, or other suitable surfactants.

In the hydrogel of the present application, a plurality of liposomes connect with each other by a plurality of single-stranded nucleotides so as to form a network, thereby obtaining a hydrogel composed of liposomes with a stable structure. At the same time, due to the stability of the liposome per se, the release control of the load material can be achieved by modifying the properties of the liposome, so that the hydrogel of the present application can achieve a slow release of the load material in the liposome. Compared with the hydrogels without liposomes in the prior art, the structure of the hydrogel of this embodiment is more stable and can release drugs under control, and therefore the hydrogel of the present application could be better applied to the external application of drugs and cosmetics. In addition, since the hydrogel of the present application has a plurality of liposomes, it can enrich a large amount of the load material in the hydrogel, thereby improving the encapsulation capacity of the hydrogel.

It should be noted that in this article, relational terms such as first and second are used only to distinguish one entity or operation from another entity or operation, and do not necessarily require or imply that there is any such actual relationship or order among these entities or operations. In the absence of more restrictions, the elements defined by the phrase "including one . . . " do not exclude that there are other identical elements in the process, method, article or equipment that includes the former elements.

According to the embodiments of the present application described above, these embodiments do not describe all the details in detail, nor limit the invention to the specific embodiments described. Obviously, according to the above description, many modifications and changes can be made. This specification selects and specifically describes these embodiments in order to better explain the principles and practical applications of the present application, so that those skilled in the art can make good use of the present application and modifications and uses based on the present application. The present application is only limited by the claims, their full scope and equivalents.

The invention claimed is:

1. A hydrogel comprising a plurality of first single-stranded nucleotides, a plurality of first liposomes, a plurality of second single-stranded nucleotides and a plurality of second liposomes, wherein the first single-stranded nucleotide and the second single-stranded nucleotide have complementary sticky ends, wherein the hydrogel includes a linker and where the linker is a cell penetrating peptide.

2. The hydrogel according to claim 1, wherein the first single-stranded nucleotide and the second single-stranded nucleotide are both single-stranded oligonucleotides.

3. The hydrogel according to claim 1, wherein the first or second liposome contains a load material.

4. The hydrogel according to claim 3, wherein the load material is a medicine or a cosmetic.

5. A method for preparing a hydrogel, including:
forming a first part by mixing a first single-stranded nucleotide with a first liposome, and forming a second part by mixing a second single-stranded nucleotide with a second liposome, wherein the first single-stranded nucleotide and the second single-stranded nucleotide have complementary sticky ends;
forming a hydrogel by mixing the first part and the second part, wherein the hydrogel includes a linker and where the linker is a cell penetrating peptide.

6. The method for preparing a hydrogel according to claim 5, wherein the first single-stranded nucleotide and the second single-stranded nucleotide are both single-stranded oligonucleotides.

7. The method for preparing a hydrogel according to claim 5, wherein before forming the first part and the second part, the method further includes:
mixing a load material with the first liposome and/or the second liposome respectively, so as to make the first liposome and/or the second liposome encapsulate the load material.

8. The method for preparing a hydrogel according to claim 7, wherein the load material is a medicine or a cosmetic.

9. The method for preparing a hydrogel according to claim 7, wherein after forming the hydrogel, the method further includes:
releasing at least part of the load material from the first liposome and the second liposome by adding a surfactant to the hydrogel.

10. The method for preparing a hydrogel according to claim 5, wherein said forming the first part and forming the second part include:
mixing the first single-stranded nucleotide, the first liposome and a linker, and connecting the first single-stranded nucleotide with the first liposome through the linker to obtain the first part; mixing the second single-stranded nucleotide, the second liposome and a linker, and connecting the second single-stranded nucleotide with the second liposome through the linker to obtain the second part.

11. The method for preparing a hydrogel according to claim 10, wherein the linker is a cell-penetrating peptide.

* * * * *